(12) United States Patent
Winniczuk

(10) Patent No.: US 7,226,610 B2
(45) Date of Patent: Jun. 5, 2007

(54) COMPOSITIONS AND METHODS FOR THE TREATMENT AND PREVENTION OF DISEASE IN PLANTS

(75) Inventor: Paul Winniczuk, Auburndale, FL (US)

(73) Assignee: Preservation Sciences, Inc., St. Petersburg, FL (US)

( * ) Notice: Subject to any disclaimer, the term of this patent is extended or adjusted under 35 U.S.C. 154(b) by 0 days.

(21) Appl. No.: 11/093,501

(22) Filed: Mar. 30, 2005

(65) Prior Publication Data

US 2006/0222674 A1    Oct. 5, 2006

(51) Int. Cl.
*A01N 25/08*    (2006.01)
*A01N 27/00*    (2006.01)

(52) U.S. Cl. ............... 424/405; 424/407; 514/724; 514/725; 514/726; 514/727; 514/730; 514/731; 514/732; 514/733; 514/734; 514/735; 514/736; 514/737; 514/739; 514/763

(58) Field of Classification Search ............ None
See application file for complete search history.

(56) References Cited

U.S. PATENT DOCUMENTS

| | | | | |
|---|---|---|---|---|
| 2,938,028 | A | * | 5/1960 | Platt et al. .................. 426/651 |
| 5,843,215 | A | * | 12/1998 | Whalon et al. ......... 106/18.29 |
| 5,935,272 | A | * | 8/1999 | Mahaffey et al. .............. 8/403 |
| 6,482,455 | B1 | * | 11/2002 | Freire et al. ................ 426/310 |
| 2004/0161517 | A1 | * | 8/2004 | Winniczuk .................. 426/532 |
| 2004/0248764 | A1 | * | 12/2004 | Franklin ........................ 514/1 |

* cited by examiner

*Primary Examiner*—Neil S. Levy
(74) *Attorney, Agent, or Firm*—Kramer Levin Naftalis & Frankel LLP

(57) ABSTRACT

Non-toxic, naturally derived and economical compositions for treating and preventing bacterial or fungal disease in plants, especially citrus canker, wherein such compositions include various combinations of d-limonene, wax and monohydric alcohol are provided. Methods for making and using such compositions are also provided.

5 Claims, No Drawings ically limits the amount of pesticide that can be applied and the timing of
COMPOSITIONS AND METHODS FOR THE TREATMENT AND PREVENTION OF DISEASE IN PLANTS

FIELD OF THE INVENTION

The present invention relates to compositions and methods for the treatment and prevention of bacterial and fungal disease in plants. Among the important diseases which can be treated and prevented by the present invention is citrus canker.

BACKGROUND OF THE INVENTION

As reported by the University of Florida Plant Pathology Department, fungal and bacterial pathogens can lower yields, reduce quality, negatively affect the aesthetic and economic value and even ultimately destroy plants, crops, pre-harvest fruits, trees, vegetables and grasses. In particular, bacterial and fungal diseases in citrus plants create huge economic burdens on the citrus industry worldwide. Citrus canker alone causes severe economic consequences in the world's citrus growing regions. The bacteria which causes citrus canker, *Xanthomonas campestris* pv. *citri*, has been found in southern Asia, Japan, the Middle East, Africa, South America and now North America. Historically, citrus canker outbreaks have occurred in North America in the early 1900s and again in 1986. Fortunately, through the use of aggressive eradication techniques, the disease was eliminated in both instances. Citrus canker, however, can be reintroduced when people inadvertantly transport infected citrus fruits and seedlings into citrus growing areas in the U.S. and elsewhere. In the U.S., Florida is by far the state most at risk from citrus canker given its combination of high humidity throughout the year, seasonal hurricanes and frequent thunderstorms accompanied by high wind gusts. (See The University of Florida Plant Pathology Department Report at www.biotech.ufl.edu/PlantContainment/canker.htm)

The University of Florida Extension Service reports that in 1995 citrus canker was again detected in the U.S. in citrus trees in the Miami-Dade County, Florida area. Citrus canker then spread to the commercial groves in southwest Florida. Since 1998 more than 870,000 trees have been destroyed in conjunction with-eradication programs. (See http://edis.ifas.ufl.edu/FE286)

Costs in managing the threat of citrus canker include capital investment for spray equipment, the lost value of affected fruit, costs associated with inspection and eradication, and costs associated with the creation of natural windbreaks and other defensive tactics. Current spraying programs include relatively expensive copper based sprays. The University of Florida Extension Service has estimated that if citrus canker became endemic in Florida, the total cost for countering endemic citrus canker, including the use of copper based sprays, could be more than $300 per acre.

Many types of organic molecules possess antimicrobial properties and can be used to effectively control fungal and bacterial disease in plants. However, many of the currently used pesticides are toxic to humans, animals and the exposed environment which limits large scale application in, for example, citrus orchards. The Environmental Protection Act was established in 1972, in part, to address concerns over the use of potentially toxic materials to control or treat diseases in crops. In 1996 Congress passed the Food Quality Protection Act requiring the Environmental Protection Agency to reassess the safety and efficacy of every existing pesticide by 2006. Concerns about pesticide residues on plants and the exposure of field workers to such residues severely limits the amounts of pesticide that can be applied and the timing of such application. These limitations decrease the potential effectiveness of commonly used pesticides to prevent and treat bacterial and fungal disease in plants in general and citrus canker in particular.

Accordingly, there exists a tremendous need for effective, economical and non-toxic compositions and methods for preventing and treating bacterial and fungal disease in plants. In particular there is a tremendous need for effective, economical and non-toxic compositions and methods for preventing and treating citrus canker.

SUMMARY OF THE INVENTION

The present invention relates to compositions and methods which prevent and treat bacterial and fungal disease in plants. More particularly, the present invention is effective in preventing and treating citrus canker caused by the bacteria *Xanthomonas campestris* pv. *citri*. The compositions of the present invention include combinations of wax, d-limonene and monohydric alcohol. Applicants have unexpectedly found that combinations of these and similar ingredients provide compositions that are capable of preventing and treating bacterial and fungal disease in plants, including citrus canker.

Moreover, compositions according to the present invention do not include toxic chemicals or chemicals at toxic levels. Accordingly, there are minimal regulatory limitations for the use of such compositions.

The present invention also provides methods of making and using such compositions. In one embodiment, a method of this invention includes the steps of (1) heating water; (2) adding monohydric alcohol to the water and mixing; (3) adding d-limonene to the mixture and mixing further; (4) adding wax to the mixture and mixing further; (5) optionally filtering the mixture; and (6) optionally cooling the mixture.

Accordingly, one object of the present invention is to provide compositions for preventing and treating bacterial and fungal disease in citrus trees, especially citrus canker, comprising various combinations of wax, d-limonene, and monohydric alcohol.

Another object of the present invention is to provide methods of making compositions for preventing and treating bacterial and fungal disease in citrus trees, especially citrus canker.

A further object of the present invention is to provide methods of preventing and treating disease in citrus trees, including citrus canker, which include applying particular compositions to citrus trees.

DETAILED DESCRIPTION OF THE INVENTION

The present invention provides non-toxic, naturally-derived compositions which treat and prevent bacterial and fungal diseases in citrus trees, espcially citrus canker caused by the bacteria *Xanthomonas campestris* pv. *citri*.

The compositions of the present invention may comprise wax, d-limonene and monohydric alcohol. Applicants have unexpectedly found that combinations of these and similar ingredients provide compositions which are capable of treating and preventing bacterial and fungal disease in plants, especially citrus canker.

As used herein, unless otherwise stated, percentage amounts of an ingredient are by total weight of the composition in which that ingredient is included. Compositions of the present invention may include wax material. The preferred wax material is beeswax. Beeswax may comprise from about 0.005 to about 10.0%, preferably from about 0.1 to about 5.0%, and more preferably from about 1.0 to about 2.0% and even more preferably about 1.5% of the composition. Optionally, as a substitute for, or in addition to beeswax, the compositions of the present invention may include benzoic acid, salicylic acid and paraffin, alone or in various combinations, in amounts by weight totaling those given above for beeswax alone. Beeswax, benzoic acid, salicylic acid and paraffin are commercially available from many sources.

Compositions of the present invention may also include d-limonene. D-limonene is the major component of the oil extracted from citrus rind. D-limonene has been used extensively as an ingredient in cleaning products. D-limonene in compositions according to the present invention may comprise from about 0.5% to about 20.0%, preferably from about 5.0% to about 15.0%, and more preferably from about 9.0% to about 11.0%. D-limonene is commercially available from many sources.

Compositions of the present invention may also include monohydric alcohols such as methanol, ethanol and butanol, alone or in various combinations. A preferred monohydric alcohol is ethanol. A preferred combination of monohydric alcohols includes ethanol and methanol. Monohydric alcohols according to the present invention may be either denatured or non-denatured. The monohydric alcohol may comprise from about 0.5% to about 15.0%, more preferably about 2.0 to about 12.0%, and even more preferably from about 4.0 to about 9.0% of the composition. Monohydric alcohols are commercially available from many sources.

Compositions of the present invention also may include other excipients. Other excipients may include potassium hydroxide, xanthan gum, and hydrochloric acid. Potassium hydroxide and hydrochloric acid may be used to control and adjust pH levels. Xanthan gum may be used to control and adjust viscosity and also provide product stability. When included in compositions according to the present invention, potassium hydroxide may comprise from about 0.01 to about 5.0%, more preferably from about 0.05% to about 2.0%, and even more preferably from about 0.1 to about 0.5% of the composition. When included in compositions according to the present invention, xanthan gum may comprise from about 0.01 to about 2.0%, preferably from about 0.01 to about 1.0%, and more preferably from about 0.1 to about 0.5% of the composition.

The balance of the composition may comprise water. The water may be purified and, if so, preferably has a bacterial colony count of less than about 100 colonies per ml. The amount of water used may be varied based on the desired concentration of the composition. The water may be made alkaline by the addition of potassium hydroxide and preferably has a pH above about 10.0. The preferred water hardness is less than 1 grain per gallon or less than 50 ppm.

Methods of Making

The present invention also provides methods of making the compositions described herein. Such methods may include the steps of (1) adding monohydric alcohol to water and mixing; (2) heating the alcohol and water mixture; (3) adding d-limonene and mixing; (4) heating the monohydric alcohol, d-limonene and water combination; (5) adding wax and mixing further; (6) heating the monohydric alcohol, d-limonene, wax and water mixture; (7) optionally filtering the mixture; and (8) optionally cooling the filtrate.

In another embodiment the method of making compositions includes the steps of (1) adding potassium hydroxide to water and mixing; (2) adding monohydric alcohol (e.g., ethanol) to the water and mixing; (3) heating the potassium hydroxide, alcohol, and water mixture to about 175° F. for five minutes or less; (4) adding d-limonene to the water and mixing, while maintaining the temperature at about 175° F. for about 15 minutes (4) adding beeswax to the water and mixing, while maintaining the temperature at about 170° F. for about 15 minutes; (5) adding xanthan gum and mixing vigorously while allowing the mixture to cool; (6) filtering the cooled mixture.

It should be noted that the order of steps recited above in embodiments of the present invention may be varied to produce compositions according to the present invention. For example, d-limonene may be added prior to adding monohydric alcohol or wax could be added before either d-limonene or monohydric alcohol.

In certain examples of embodiments of the present invention, the water may be heated in any heating step (if the particular method of making the composition includes such) to between about 110° to about 272° F., preferably to between about 130° to about 210° F., and more preferably to between about 165° to about 180 F.

The liquid mixture may then be pumped through filters at a pressure sufficient to effectively collect the composition. The filtering pressure may be from about 5 to about 100 psi, preferably is from about 10 to about 40 psi, and more preferably is about 30 psi. The composition may be cooled before use. Preferably the composition may be cooled to at least about 95° F. Cooling may be facilitated by the use of a heat exchanger.

Compositions according to the present invention may also be formed into a crystalline powder form to facilitate packaging, storage and use. This may be achieved, for example, by reducing the water content to about 10% of the composition, adding xanthan gum and gum arabic in roughly equal amounts, drying the composition, and then grinding to break up larger particles. Drying may be achieved by, for example, a vacuum drier, a fluidized bed drier, a low temperature roller drier, a vacuum extrusion drier or by other drying means.

Methods of Using

The present invention also includes methods of using compositions which can prevent and treat bacterial and fungal diseases in plants, espcially citrus canker. An effective amount of the compositions of the present invention can be applied to, for example, citrus trees. In this context an effective amount means an amount that is sufficient to prevent and reduce bacterial or fungal disease affecting citrus trees. Accordingly, an effective amount can vary depending on whether the primary purpose prevention or treatment, and if the latter, the severity of the disease state. In general, however, the compositions of the present invention may be effectively applied to citrus trees in a concentration ranging from about 1% to about 80%. Preferably, the concentration will be between 10% and 50% and more preferably between 20% and 40%.

Compositions according to the present invention can be sprayed onto trees without any observable disease using conventional spray equipment. Likewise, these compostions can be sprayed onto diseased trees in the same manner. For use in diseased trees, the concentration of compositions according to the present invention generally will be higher than for preventative treatments.

Compositions of the present invention may reduce or eliminate the growth of a wide range of disease-causing organisms in plants, including citrus trees. These compositions have been shown to be especially effective in the treatment and prevention of citrus canker caused by *Xanthomonas campestris* pv. *citri*.

EXAMPLE

The composition as shown in Table 1 was used to demonstrate the effectiveness of an exemplary embodiment of the present invention in treating citrus canker:

TABLE 1

| | |
|---|---|
| monohydric alcohol (ethanol) | 6.65% |
| d-limonene | 10.00% |
| beeswax | 1.47% |
| water | 81.40 |
| potassium hydroxide | 0.16% |
| xanthan gum | 0.16% |

Ten citrus trees with existing canker lesions were drench sprayed with a 25% solution of the composition according to Table 1, while ten citrus trees were used as controls. Tree limbs were tagged with strips of caution tape to facilitate precise identification of the treatment trees. Weekly observations were taken to determine the effect of the treatment on the canker lesions. A second treatment was applied approximately two weeks after the first. Over the course of eight weeks of observation, canker lesions had not expanded on the ten treatment trees, while canker lesions had grown substantially on the ten control trees. The treatment trees and control trees both exhibited similar insubstantial levels of leaf wilting and fruit drop.

What is claimed is:

1. A method of reducing the incidence of disease in a plant species comprising applying to said plant species a composition which comprises from about 0.5% to about 15% monohydric alcohol, from about 0.5% to about 20% d-limonene, and from about 0.005% to about 10% wax or wax extract, all of which percentages are expressed by weight of the composition prior to diluting the composition or converting the composition to a non-liquid form.

2. The method of claim 1, wherein the wax or wax extract is derived from beeswax.

3. The method of claim 1, wherein the monohydric alcohol is selected from the group consisting of ethanol, methanol and butanol, alone or in any combination.

4. The method of claim 1, wherein the plant species is a citrus tree.

5. The method of claim 4, wherein the disease is citrus canker.

* * * * *